(12) United States Patent
Abouabdellah et al.

(10) Patent No.: US 7,645,757 B2
(45) Date of Patent: Jan. 12, 2010

(54) DERIVATIVES OF HETEROARYL-ALKYLCARBAMATES, METHODS FOR THEIR PREPARATION AND USE THEREOF AS FATTY ACID AMIDO HYDROLASE ENZYME INHIBITORS

(75) Inventors: Ahmed Abouabdellah, Thiais (FR); Regine Bartsch-Li, Fontenay-aux-Roses (FR); Christian Hoornaert, Antony (FR); Antoine Ravet, Paris (FR)

(73) Assignee: sanofi-aventis, Paris (FR)

( * ) Notice: Subject to any disclaimer, the term of this patent is extended or adjusted under 35 U.S.C. 154(b) by 133 days.

(21) Appl. No.: 11/464,355

(22) Filed: Aug. 14, 2006

(65) Prior Publication Data

US 2007/0021426 A1     Jan. 25, 2007

Related U.S. Application Data

(63) Continuation of application No. PCT/FR2005/000451, filed on Feb. 25, 2005.

(30) Foreign Application Priority Data

Feb. 26, 2004    (FR)  ................... 04 01949

(51) Int. Cl.
    A61K 31/501     (2006.01)
    A61K 31/541     (2006.01)
    A61K 31/5355    (2006.01)
    A61K 31/55      (2006.01)
    C07D 417/04     (2006.01)
    C07D 401/04     (2006.01)
    C07D 403/04     (2006.01)
    C07D 405/04     (2006.01)
    C07D 409/04     (2006.01)
    C07D 413/04     (2006.01)
    A61P 29/00      (2006.01)
    A61P 9/00       (2006.01)
    A61P 3/00       (2006.01)

(52) U.S. Cl. .................. 514/252.02; 514/256; 544/335; 544/224; 544/242; 546/335; 546/147; 546/175; 546/113; 546/272.1; 546/271.4; 546/121; 548/340.1; 548/226; 548/375.1; 548/131; 548/309.7; 548/507; 548/561; 548/204; 548/247; 562/555

(58) Field of Classification Search ............... 544/295, 544/296, 333, 335, 224, 242; 514/256, 252.02; 546/312

See application file for complete search history.

(56) References Cited

U.S. PATENT DOCUMENTS 2,866,734 A    12/1958 Shapro et al.
3,054,794 A    9/1962 Shapiro et al.
3,876,661 A    4/1975 Verbiscar et al.

FOREIGN PATENT DOCUMENTS

WO    WO 99/26584        6/1999
WO    WO 02/087569       11/2002
WO    WO 2004/020430     3/2004
WO    WO 2004/067498     8/2004

OTHER PUBLICATIONS

Griesser Chapter 8, The Importance of Solvates (pp. 211-230), in the text, Polymorphism: In the Pharmaceutical Industry, Hilfiker, 2006.*
Brittain, Chapter V of Polymorphism in Pharmaceutical Solids, 1999, pp. 126-127.*
Jayamanne, et al., Brit. J. Pharmacol. (2006) 147, 281-288.*
Paylor, et al., Pharmacolog. Res., vol. 54, # 6, Dec. 2006, pp. 481-485.*
Murillo-Rodriguez, et al., Euro. J. Pharmacol. 2007;562(1-2):82-91 (abst).*
Batkai, et al., Circulation. 2004;110:1996-2002.*
Sipe, et al., Int. J. Obes., Jul. 2005; 29(7): 755-9 (abst.).*
Day, et al., Mol. Pharmacol., 59:1369-1375, 2001.*
Nat. Inst. of Neurological Disorders and Stroke, 2009.*
Grazia Cascio, M., et. al., A Structure-Activity Relationship Study on N-Arachidonoyl-Amino Acids as Possible Endogenous Inhibitors of Fatty Acid Amide Hydrolase, Biochemical and Biophysical Research Communications vol. 314, (2004) pp. 192-196.
Shapiro, S.L., et. al., Aminoalkylamides and Oxazolidinedionos, Journal of the American Chemical Society, vol. 81, No. 12, (1959) pp. 3083-3088.
Tarzia, G., et. al., Design, Synthesis, and Structure-Activity Relationships of Alkylcarbamic Acid Aryl Esters, A New Class of Fatty Acid Amide Hydrolase Inhibitors, J. Med. Chem. 2003 vol. 46, pp. 2352-2360.

* cited by examiner

Primary Examiner—Mark L Berch
Assistant Examiner—Cecilia M Jaisle
(74) Attorney, Agent, or Firm—Balaram Gupta

(57) ABSTRACT

The present invention is directed to compounds and compositions for the treatment of neurological diseases that cause neurogenic and neuropathic pain, inflammatory diseases, renal ishaemia, cardiovascular disease and other pathologies caused by the presence of endogenous cannabinoids and or other substrates resulting from the metabolic activities of fatty acid amido hydrolase (FAAH). These compounds are represented by the formula

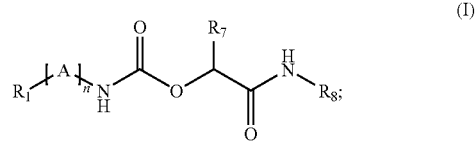

alkylene group; a salt thereof, or a hydrate or a solvate of said compound or said salt; where the variables are as defined in the attached specification.

7 Claims, No Drawings

DERIVATIVES OF HETEROARYL-ALKYLCARBAMATES, METHODS FOR THEIR PREPARATION AND USE THEREOF AS FATTY ACID AMIDO HYDROLASE ENZYME INHIBITORS

CROSS-REFERENCE TO RELATATED APPLICATIONS

This application is a continuation of International Application No. PCT/FR2005000451 filed on Feb. 25, 2005 which is incorporated herein by reference in its' entirety which also claims benefit of priority of French Patent Application No. 04/01949 filed on Feb. 26, 2004.

FIELD OF THE INVENTION

The present invention relates generally to compounds and compositions for the treatment of neurological diseases that cause neurogenic and neuropathic pain, inflammatory diseases, renal ishaemia, cardiovascular disease and other pathologies caused by the presence of endogenous cannabinoids and or other substrates resulting from the metabolic activities of fatty acid amido hydrolase (FAAH).

BACKGROUND OF THE INVENTION

Aryl- and -heteroarylalkylcarbamate derivatives are known to be useful in the treatment of numerous metabolic diseases in varying degrees. Their preparation and their application in therapeutics is also well documented.

Phenylalkylcarbamate and (dioxan-2-yl)alkylcarbamate derivatives, disclosed respectively in the documents FR 2850377 A and WO 2004/020430 A2, which are inhibitors of the enzyme FAAH (Fatty Acid Amido Hydrolase) are already known and are incorporated herein by reference.

However, there still exists a need to find and develop products which are inhibitors of the enzyme FAAH. The compounds of the present invention can readly acheve this objective.

The compounds of the invention correspond to the general formula (I):

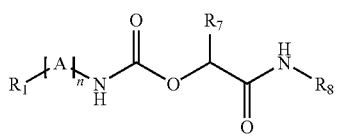

in which:

A is chosen from one or more groups X, Y and/or Z;

X represents a methylene group optionally substituted by one or two $C_{1-6}$-alkyl, $C_{3-7}$-cycloalkyl or $C_{3-7}$-cycloalkyl-$C_{1-3}$-alkylene groups;

Y represents either a $C_2$-alkenylene group optionally substituted by one or two $C_{1-6}$-alkyl, $C_{3-7}$-cycloalkyl or $C_{3-7}$-cycloalkyl-$C_{1-3}$-alkylene groups; or a $C_2$-alkynylene group;

Z represents a group of formula:

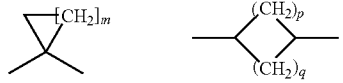

m represents an integer ranging from 1 to 5;

p and q represent integers and are defined such that p+q is a number ranging from 1 to 5;

n represents an integer ranging from 1 to 7;

$R_1$ represents an $R_2$ group optionally substituted by one or more $R_3$ and/or $R_4$ groups;

$R_2$ represents a group chosen from a pyridyl, pyrimidinyl, pyridazinyl, pyrazinyl, triazinyl, pyrrolyl, furyl, thienyl, imidazolyl, oxazolyl, thiazolyl, pyrazolyl, isoxazolyl, isothiazolyl, oxadiazolyl, thiadiazolyl, triazolyl, tetrazolyl, naphthyl, quinolinyl, tetrahydroquinolinyl, isoquinolinyl, tetrahydroisoquinolinyl, 2-oxo-3,4-dihydroquinolinyl, 1-oxo-3,4-dihydroisoquinolinyl, quinazolinyl, quinoxalinyl, phthalazinyl, cinnolinyl, naphthyridinyl, benzofuranyl, dihydrobenzofuranyl, benzothienyl, dihydrobenzothienyl, indolyl, indolinyl, indazolyl, isoindolyl, benzimidazolyl, benzoxazolyl benzisoxazolyl, benzothiazolyl, benzisothiazolyl, benzotriazolyl, benzoxadiazolyl, benzothiadiazolyl, pyrrolopyridyl, furopyridyl, thienopyridyl, imidazopyridyl, oxazolopyridyl, thiazolopyridyl, pyrazolopyridyl, isoxazolopyridyl or isothiazolopyridyl;

$R_3$ represents a group chosen from halogen atoms or cyano, nitro, $C_{1-6}$-alkyl, $C_{3-7}$-cycloalkyl, $C_{1-6}$-alkoxy, hydroxyl, $C_{1-6}$-thioalkyl, $C_{1-6}$-fluoroalkyl, $C_{1-6}$-fluoroalkoxy, $C_{1-6}$-fluorothioalkyl, $NR_5R_6$, $NR_5COR_6$, $NR_5CO_2R_6$, $NR_5SO_2R_6$, $COR_5$, $CO_2R_5$, $CONR_5R_6$, $SO_2R_5$, $SO_2NR_5R_6$, —O—($C_{1-3}$-alkylene)-O— or phenyl groups, the phenyl group optionally being substituted by one or more halogen atoms;

$R_4$ represents a group chosen from phenyl, phenyloxy, benzyloxy, naphthyl, pyridyl, pyrimidinyl, pyridazinyl or pyrazinyl groups; it being possible for the $R_4$ group or groups to be substituted by one or more $R_3$ groups which are identical to or different from one another;

$R_5$ and $R_6$ represent, independently of one another, a hydrogen atom or a $C_{1-6}$-alkyl group or form, with the atom or atoms which carry them, a ring chosen from an azetidine, pyrrolidine, piperidine, morpholine, thiomorpholine, azepine or piperazine ring, this ring optionally being substituted by a $C_{1-6}$-alkyl or benzyl group;

$R_7$ represents a hydrogen atom or a $C_{1-6}$-alkyl group;

$R_8$ represents a hydrogen atom or a $C_{1-6}$-alkyl, $C_{3-7}$-cycloalkyl or $C_{3-7}$-cycloalkyl-$C_{1-3}$-alkylene group.

In the context of the invention, the compounds of general formula (I) can thus comprise several groups A which are identical to or different from one another.

Among the compounds of general formula (I), a first subgroup of compounds is comprised of compounds for which:

A is chosen from one or more groups X and/or Y;

X represents a methylene group;

Y represents a $C_2$-alkynylene group;

n represents an integer ranging from 1 to 5;

$R_1$ represents an $R_2$ group optionally substituted by one or more $R_3$ and/or $R_4$ groups;

$R_2$ represents a group chosen from a pyridyl, pyrimidinyl, pyridazinyl, imidazolyl, oxazolyl, pyrazolyl, isoxazolyl, oxadiazolyl, naphthyl, quinolinyl, isoquinolinyl, dihydroisoquinolinyl, 2-oxo-3,4-dihydroquinolinyl, indolyl, benzimidazolyl or pyrrolopyridyl;

$R_3$ represents a group chosen from halogen atoms, more particularly chlorine and fluorine atoms, or $C_{1-6}$-alkyl, more particularly methyl, $C_{3-7}$-cycloalkyl, more particularly cyclopropyl, $C_{1-6}$-alkoxy, more particularly methoxy, $NR_5R_6$ or phenyl groups;

$R_4$ represents a group chosen from phenyl, naphthyl or pyridyl groups; it being possible for the $R_4$ group or groups to be substituted by one or more $R_3$ groups which are identical to or different from one another;

$R_5$ and $R_6$ represent, independently of one another, a $C_{1-6}$-alkyl group, more particularly a methyl;

$R_7$ represents a hydrogen atom or a $C_{1-6}$-alkyl group;

$R_8$ represents a hydrogen atom or a $C_{1-6}$-alkyl, $C_{3-7}$-cycloalkyl or $C_{3-7}$-cycloalkyl-$C_{1-3}$-alkylene group.

Among the compounds of general formula (I), a second subgroup of compounds is comprised of the compounds for which:

A, X, Y, Z, m, p, q, n, $R_1$, $R_3$, $R_4$, $R_5$, $R_6$, $R_7$ and $R_8$ are as defined in the general formula (I) or in the first subgroup as defined above, and $R_2$ represents a group chosen from a pyridyl, pyrimidinyl, oxazolyl, isoxazolyl, naphthyl, quinolinyl or isoquinolinyl.

Among the compounds of general formula (I), a third subgroup of compounds is comprised of the compounds for which:

A, X, Y, Z, m, p, q, n, $R_1$, $R_2$, $R_3$, $R_4$, $R_5$ and $R_6$ are as defined in the general formula (I) or in the subgroups as defined above;

$R_7$ represents a hydrogen atom;

$R_8$ represents a hydrogen atom or a $C_{1-6}$-alkyl group, more particularly a methyl.

The following compounds may be mentioned among the compounds of the subgroups defined above:

2-(methylamino)-2-oxoethyl (5-phenylpyrid-2-yl)methylcarbamate
2-(methylamino)-2-oxoethyl 2-(5-phenylpyrid-2-yl)ethylcarbamate
2-(methylamino)-2-oxoethyl 2-(6-phenylpyrid-3-yl)ethylcarbamate
2-(methylamino)-2-oxoethyl 2-(2-phenylpyrimidin-5-yl)ethylcarbamate
2-(methylamino)-2-oxoethyl 2-(5-phenylpyrimidin-2-yl)ethylcarbamate
2-(methylamino)-2-oxoethyl 2-[6-(4-chlorophenyl)pyrimidin-4-yl]ethylcarbamate
2-(methylamino)-2-oxoethyl 2-[6-(4-chlorophenyl)-2-methylpyrimidin-4-yl]ethylcarbamate
2-(methylamino)-2-oxoethyl 2-[6-(4-chlorophenyl)-2-(dimethylamino)pyrimidin-4-yl]ethylcarbamate
2-(methylamino)-2-oxoethyl 2-(isoquinolin-7-yl)ethylcarbamate
2-(methylamino)-2-oxoethyl 2-(2-phenyl-1,3-oxazol-4-yl)ethylcarbamate
2-(methylamino)-2-oxoethyl 2-[5-(4-chlorophenyl)isoxazol-3-yl]ethylcarbamate
2-amino-2-oxoethyl 3-(pyrid-2-yl)propylcarbamate
2-amino-2-oxoethyl 3-(pyrid-3-yl)propylcarbamate
2-amino-2-oxoethyl 3-(pyrid-4-yl)propylcarbamate
2-amino-2-oxoethyl 3-(pyrimidin-5-yl)propylcarbamate
2-(methylamino)-2-oxoethyl 3-[6-(4-chlorophenyl)pyrimidin-4-yl]propylcarbamate
2-(methylamino)-2-oxoethyl 3-[6-(4-chlorophenyl)-2-methylpyrimidin-4-yl]propylcarbamate
2-(methylamino)-2-oxoethyl 3-[6-(4-chlorophenyl)-2-(dimethylamino)pyrimidin-4-yl]propylcarbamate
2-amino-2-oxoethyl 3-(quinolin-2-yl)propylcarbamate
2-amino-2-oxoethyl 3-(quinolin-4-yl)propylcarbamate
2-amino-2-oxoethyl 3-(isoquinolin-1-yl)propylcarbamate
2-amino-2-oxoethyl 3-(isoquinolin-4-yl)propylcarbamate
2-(methylamino)-2-oxoethyl 3-[5-(4-chlorophenyl)isoxazol-3-yl]propylcarbamate
2-amino-2-oxoethyl 3-[3-(4-chlorophenyl)isoxazol-5-yl]propylcarbamate
2-(methylamino)-2-oxoethyl 3-[3-(4-chlorophenyl)isoxazol-5-yl]propylcarbamate
2-(methylamino)-2-oxoethyl 3-[3-(4-phenylphenyl)isoxazol-5-yl]propylcarbamate
2-(methylamino)-2-oxoethyl 3-[3-(naphth-2-yl)isoxazol-5-yl]propylcarbamate
2-amino-2-oxoethyl 4-(pyrid-2-yl)butylcarbamate
2-amino-2-oxoethyl 4-(pyrid-3-yl)butylcarbamate
2-amino-2-oxoethyl 4-(pyrid-4-yl)butylcarbamate
2-amino-2-oxoethyl 4-(pyrimidin-5-yl)butylcarbamate
2-(methylamino)-2-oxoethyl 4-[6-(4-chlorophenyl)pyrimidin-4-yl]butylcarbamate
2-(methylamino)-2-oxoethyl 4-[6-(4-chlorophenyl)-2-methylpyrimidin-4-yl]butylcarbamate
2-(methylamino)-2-oxoethyl 4-[6-(4-chlorophenyl)-2-cyclopropylpyrimidin-4-yl]butylcarbamate
2-(methylamino)-2-oxoethyl 4-[6-(4-chlorophenyl)-2-(dimethylamino)pyrimidin-4-yl]butylcarbamate
2-amino-2-oxoethyl 4-(quinolin-2-yl)butylcarbamate
2-amino-2-oxoethyl 4-(quinolin-4-yl)butylcarbamate
2-amino-2-oxoethyl 4-(isoquinolin-1-yl)butylcarbamate
2-amino-2-oxoethyl 4-(isoquinolin-4-yl)butylcarbamate
2-(methylamino)-2-oxoethyl 4-[5-(4-chlorophenyl)isoxazol-3-yl]butylcarbamate
2-(methylamino)-2-oxoethyl 4-[3-(4-chlorophenyl)isoxazol-5-yl]butylcarbamate
2-(methylamino)-2-oxoethyl 4-[3-(4-phenylphenyl)isoxazol-5-yl]butylcarbamate
2-(methylamino)-2-oxoethyl 4-[3-(naphth-2-yl)isoxazol-5-yl]butylcarbamate
2-amino-2-oxoethyl 5-(pyrid-2-yl)pentylcarbamate
2-amino-2-oxoethyl 5-(pyrid-4-yl)pentylcarbamate
2-amino-2-oxoethyl 5-(pyrimidin-5-yl)pentylcarbamate
2-amino-2-oxoethyl 5-(quinolin-2-yl)pentylcarbamate
2-amino-2-oxoethyl 5-(quinolin-4-yl)pentylcarbamate
2-amino-2-oxoethyl 5-(isoquinolin-1-yl)pentylcarbamate
2-amino-2-oxoethyl 5-(isoquinolin-4-yl)pentylcarbamate
2-amino-2-oxoethyl [3-(naphth-1-yl)prop-2-yn-1-yl]carbamate
2-(methylamino)-2-oxoethyl [3-(naphth-1-yl)prop-2-yn-1-yl]carbamate
2-amino-2-oxoethyl [5-(naphth-1-yl)pent-4-yn-1-yl]carbamate
2-(methylamino)-2-oxoethyl [5-(naphth-1-yl)pent-4-yn-1-yl]carbamate
2-(methylamino)-2-oxoethyl [5-(4-fluoronaphth-1-yl)pent-4-yn-1-yl]carbamate
2-(methylamino)-2-oxoethyl [3-(pyrid-3-yl)isoxazol-5-ylpropyl]carbamate
2-(methylamino)-2-oxoethyl [3-(4-methoxynaphth-1-yl)isoxazol-5-ylpropyl]carbamate.

Among the compounds of general formula (I), one subfamily of compounds is comprised of the compounds corresponding to the general formula (I'):

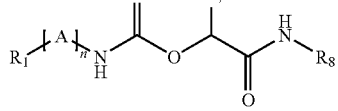

in which

A is chosen from one or more groups X, Y and/or Z;

X represents a methylene group optionally substituted by one or two $C_{1-6}$-alkyl, $C_{3-7}$-cycloalkyl or $C_{3-7}$-cycloalkyl-$C_{1-3}$-alkylene groups;

Y represents either a $C_2$-alkenylene group optionally substituted by one or two $C_{1-6}$-alkyl, $C_{3-7}$-cycloalkyl or $C_{3-7}$-cycloalkyl-$C_{1-3}$-alkylene groups; or a $C_2$-alkynylene group;

Z represents a group of formula:

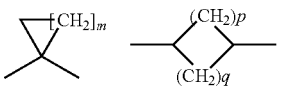

m represents an integer ranging from 1 to 5;

p and q represent integers and are defined such that p+q is a number ranging from 1 to 5;

n represents an integer ranging from 1 to 7;

$R_1$ represents an $R_2$ group optionally substituted by one or more $R_3$ and/or $R_4$ groups;

$R_2$ represents a group chosen from a pyridyl, pyrimidinyl, pyridazinyl, pyrazinyl, triazinyl, pyrrolyl, furyl, thienyl, imidazolyl, oxazolyl, thiazolyl, pyrazolyl, isoxazolyl, isothiazolyl, oxadiazolyl, thiadiazolyl, triazolyl, tetrazolyl, naphthyl, quinolinyl, tetrahydroquinolinyl, isoquinolinyl, tetrahydroisoquinolinyl, 2-oxo-3,4-dihydroquinolinyl, 1-oxo-3,4-dihydroisoquinolinyl, quinazolinyl, quinoxalinyl, phthalazinyl, cinnolinyl, naphthyridinyl, benzofuranyl, dihydrobenzofuranyl, benzothienyl, dihydrobenzothienyl, indolyl, indolinyl, indazolyl, isoindolyl, benzimidazolyl, benzoxazolyl, benzisoxazolyl, benzothiazolyl, benzisothiazolyl, benzotriazolyl, benzoxadiazolyl, benzothiadiazolyl, pyrrolopyridyl, furopyridyl, thienopyridyl, imidazopyridyl, oxazolopyridyl, thiazolopyridyl, pyrazolopyridyl, isoxazolopyridyl or isothiazolopyridyl;

$R_3$ represents a group chosen from halogen atoms or cyano, nitro, $C_{1-6}$-alkyl, $C_{1-6}$-alkoxy, hydroxyl, $C_{1-6}$-thioalkyl, $C_{1-6}$-fluoroalkyl, $C_{1-6}$-fluoroalkoxy, $C_{1-6}$-fluorothioalkyl, $NR_5R_6$, $NR_5COR_6$, $NR_5CO_2R_6$, $NR_5SO_2R_6$, $COR_5$, $CO_2R_5$, $CONR_5R_6$, $SO_2R_5$, $SO_2NR_5R_6$ or —O—($C_{1-3}$-alkylene)-O— groups;

$R_4$ represents a group chosen from phenyl, phenyloxy, benzyloxy, naphthyl, pyridyl, pyrimidinyl, pyridazinyl or pyrazinyl groups; it being possible for the $R_4$ group or groups to be substituted by one or more $R_3$ groups which are identical to or different from one another;

$R_5$ and $R_6$ represent, independently of one another, a hydrogen atom or a $C_{1-6}$-alkyl group or form, with the atom or atoms which carry them, a ring chosen from an azetidine, pyrrolidine, piperidine, morpholine, thiomorpholine, azepine or piperazine ring, this ring optionally being substituted by a $C_{1-6}$-alkyl or benzyl group;

$R_7$ represents a hydrogen atom or a $C_{1-6}$-alkyl group;

$R_8$ represents a hydrogen atom or a $C_{1-6}$-alkyl, $C_{3-7}$-cycloalkyl or $C_{3-7}$-cycloalkyl-$C_{1-3}$-alkylene group.

Among the compounds of general formula (I'), a first subgroup of compounds is comprised of the compounds for which:

A is chosen from one or more groups X and/or Y;

X represents a methylene group;

Y represents a $C_2$-alkynylene group;

n represents an integer ranging from 1 to 5;

$R_1$ represents an $R_2$ group optionally substituted by one or more phenyl groups, more particularly by one phenyl;

$R_2$ represents a group chosen from a pyridyl, pyrimidinyl, pyridazinyl, imidazolyl, oxazolyl, oxadiazolyl, naphthyl, quinolinyl, isoquinolinyl, dihydroisoquinolinyl, 2-oxo-3,4-dihydroquinolinyl, indolyl, benzimidazolyl or pyrrolopyridyl;

$R_7$ represents a hydrogen atom or a $C_{1-6}$-alkyl group;

$R_8$ represents a hydrogen atom or a $C_{1-6}$-alkyl, $C_{3-7}$-cycloalkyl or $C_{3-7}$-cycloalkyl-$C_{1-3}$-alkylene group.

Among the compounds of general formula (I'), a second subgroup of compounds is comprised of the compounds for which:

A, n and $R_1$ are as defined in the first subgroup defined above;

$R_7$ represents a hydrogen atom;

$R_8$ represents a hydrogen atom or a $C_{1-6}$-alkyl group, more particularly a methyl.

Mention may be made, among the compounds of general formula (I'), of the following compounds:

2-(methylamino)-2-oxoethyl (5-phenylpyrid-2-yl)methylcarbamate 2-(methylamino)-2-oxoethyl 2-(5-phenylpyrid-2-yl)ethylcarbamate 2-(methylamino)-2-oxoethyl 2-(6-phenylpyrid-3-yl)ethylcarbamate 2-(methylamino)-2-oxoethyl 2-(6-phenylpyridazin-3-yl)ethylcarbamate 2-(methylamino)-2-oxoethyl 2-(2-phenylpyrimidin-5-yl)ethylcarbamate 2-(methylamino)-2-oxoethyl 2-(5-phenylpyrimidin-2-yl)ethylcarbamate 2-(methylamino)-2-oxoethyl 2-(isoquinolin-7-yl)ethylcarbamate 2-(methylamino)-2-oxoethyl 2-(4-phenyl-1H-imidazol-1-yl)ethylcarbamate 2-(methylamino)-2-oxoethyl 2-(2-phenyl-1,3-oxazol-4-yl)ethylcarbamate 2-(methylamino)-2-oxoethyl 2-(5-phenyl-1,2,4-oxadiazol-3-yl)ethylcarbamate 2-amino-2-oxoethyl 3-(pyrid-2-yl)propylcarbamate 2-amino-2-oxoethyl 3-(pyrid-3-yl)propylcarbamate 2-amino-2-oxoethyl 3-(pyrid-4-yl)propylcarbamate 2-amino-2-oxoethyl 3-(pyrimidin-5-yl)propylcarbamate 2-amino-2-oxoethyl 3-(quinolin-2-yl)propylcarbamate 2-amino-2-oxoethyl 3-(quinolin-4-yl)propylcarbamate 2-amino-2-oxoethyl 3-(isoquinolin-1-yl)propylcarbamate 2-amino-2-oxoethyl 3-(isoquinolin-4-yl)propylcarbamate 2-(methylamino)-2-oxoethyl 3-(4-phenyl-1H-imidazol-1-yl)propylcarbamate 2-(methylamino)-2-oxoethyl 3-(1H-benzimidazol-1-yl)propylcarbamate 2-amino-2-oxoethyl 4-(pyrid-2-yl)butylcarbamate 2-amino-2-oxoethyl 4-(pyrid-3-yl)butylcarbamate 2-amino-2-oxoethyl 4-(pyrid-4-yl)butylcarbamate 2-amino-2-oxoethyl 4-(pyrimidin-5-yl)butylcarbamate 2-amino-2-oxoethyl 4-(quinolin-2-yl)butylcarbamate 2-amino-2-oxoethyl 4-(quinolin-4-yl)butylcarbamate 2-amino-2-oxoethyl 4-(isoquinolin-1-yl)butylcarbamate 2-amino-2-oxoethyl 4-(isoquinolin-4-yl)butylcarbamate 2-(methylamino)-2-oxoethyl 4-(1H-benzimidazol-1 -yl)butylcarbamate 2-amino-2-oxoethyl 4-(1H-indol-1-yl)butylcarbamate 2-(methylamino)-2-oxoethyl 4-(1H-indol-1-yl)butylcarbamate 2-amino-2-oxoethyl 4-(1H-pyrrolo[2,3-b]pyrid-1-yl)butylcarbamate 2-(methylamino)-2-oxoethyl 4-(1H-pyrrolo[2,3-b]pyrid-1-yl)butylcarbamate 2-(methylamino)-2-oxoethyl 4-(3,4-dihydroisoquinolin-2(1H)-yl)butylcarbamate 2-amino-2-oxoethyl 4-(2-oxo-3,4-dihydroquinolin-1(2H)-yl)butylcarbamate 2-(methylamino)-2-oxoethyl 4-(2-oxo-3,4-dihydroquinolin-1(2H)-yl)butylcarbamate 2-amino-2-oxoethyl 5-(pyrid-2-yl)pentylcarbamate
2-amino-2-oxoethyl 5-(pyrid-4-yl)pentylcarbamate
2-amino-2-oxoethyl 5-(pyrimidin-5-yl)pentylcarbamate
2-amino-2-oxoethyl 5-(quinolin-2-yl)pentylcarbamate
2-amino-2-oxoethyl 5-(quinolin-4-yl)pentylcarbamate
2-amino-2-oxoethyl 5-(isoquinolin-1-yl)pentylcarbamate
2-amino-2-oxoethyl 5-(isoquinolin-4-yl)pentylcarbamate
2-amino-2-oxoethyl [3-(naphth-1-yl)prop-2-yn-1-yl]carbamate
2-(methylamino)-2-oxoethyl [3-(naphth-1-yl)prop-2-yn-1-yl]carbamate
2-amino-2-oxoethyl [5-(naphth-1-yl)pent-4-yn-1-yl]carbamate
2-(methylamino)-2-oxoethyl [5-(naphth-1-yl)pent-4-yn-1-yl]carbamate.

The compounds of general formula (I) can comprise one or more asymmetric carbons. They can exist in the form of enantiomers or of diastereoisomers. These enantiomers and diastereoisomers, and their mixtures, including the racemic mixtures, form part of the invention.

The compounds of formula (I) can exist in the form of bases or of addition salts with acids.

Such addition salts form part of the invention.

These salts are advantageously prepared with pharmaceutically acceptable acids but the salts of other acids, of use, for example, for the purification or the isolation of the compounds of formula (I), also form part of the invention.

The compounds of general formula (I) can exist in the form of hydrates or of solvates, namely in the form of combinations or of associations with one or more molecules of water or with a solvent. Such hydrates and solvates also form part of the invention.

In the context of the invention:

$C_{t-z}$, where t and z can take the values from 1 to 7, is understood to mean a carbon chain which can have from t to z carbon atoms, for example $C_{1-3}$ a carbon chain which can have from 1 to 3 carbon atoms;

alkyl is understood to mean a saturated, linear or branched, aliphatic group; for example a $C_{1-6}$-alkyl group represents a linear or branched carbon chain of 1 to 6 carbon atoms, more particularly a methyl, ethyl, propyl, isopropyl, butyl, isobutyl, tert-butyl, pentyl or hexyl;

alkylene is understood to mean a saturated, linear or branched, divalent alkyl group, for example a $C_{1-3}$-alkylene group represents a linear or branched divalent carbon chain of 1 to 3 carbon atoms, more particularly a methylene, ethylene, 1-methylethylene or propylene;

cycloalkyl is understood to mean a cyclic alkyl group, for example a $C_{3-7}$-cycloalkyl group represents a cyclic carbon group of 3 to 7 carbon atoms, more particularly a cyclopropyl, cyclobutyl, cyclopentyl, cyclohexyl or cycloheptyl;

alkenylene is understood to mean an unsaturated divalent aliphatic group comprising 2 carbons, more particularly an ethenylene;

$C_2$-alkynylene is understood to mean a —C≡C— group;

alkoxy is understood to mean an —O-alkyl group comprising a saturated, linear or branched, aliphatic chain;

thioalkyl is understood to mean an —S-alkyl group comprising a saturated, linear or branched, aliphatic chain;

fluoroalkyl is understood to mean an alkyl group, one or more hydrogen atoms of which have been substituted by a fluorine atom;

fluoroalkoxy is understood to mean an alkoxy group, one or more hydrogen atoms of which have been substituted by a fluorine atom;

fluorothioalkyl is understood to mean a thioalkyl group, one or more hydrogen atoms of which have been substituted by a fluorine atom;

halogen is understood to mean a fluorine, a chlorine, a bromine or an iodine.

The compounds of the invention can be prepared according to various methods illustrated by the schemes which follow.

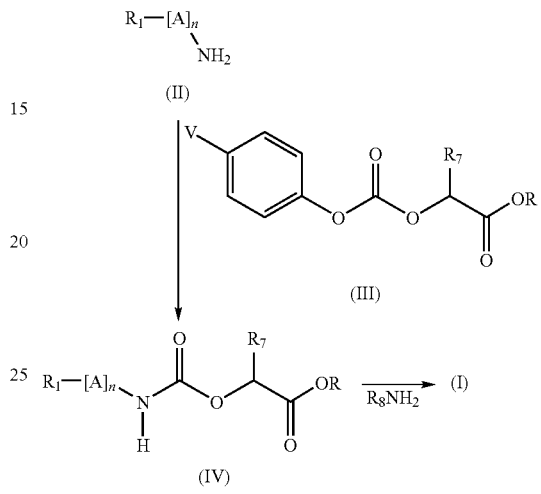

A first method (Scheme 1) for producing the compounds of general formula (I) consists in reacting an amine of general formula (II), in which $R_1$, A and n are as defined in the general formula (I), with a carbonate of general formula (III) in which V represents a hydrogen atom or a nitro group, $R_7$ is as defined in the general formula (I) and R represents a methyl or ethyl group. The carbamate-ester of general formula (IV) thus obtained is subsequently converted to the compound of general formula (I) by aminolysis using an amine of general formula $R_8NH_2$, where $R_8$ is as defined in the general formula (I). The aminolysis reaction can be carried out in a solvent, such as methanol or ethanol, or a mixture of solvents, such as methanol and tetrahydrofuran.

Another method (Scheme 2) for producing the compounds of general formula (I) consists in reacting a derivative of general formula (V), in which $R_1$, n and A are as defined in the general formula (I) and W represents a hydroxyl, mesylate or tosylate group or a chlorine, bromine or iodine atom, with an oxazolidinedione of general structure (VI), in which $R_7$ is as defined in the general formula (I), to provide the oxazolidinedione derivative of general structure (VII).

In the case where W represents a hydroxyl group, the reaction can be carried out according to the conditions of Mitsunobu (Synthesis, 1981, 1-28), for example, by the action of diethyl or diisopropyl azodicarboxylate in the presence of triphenylphosphine. In the case where W represents a chlorine, bromine or iodine atom or a mesylate or tosylate group, the reaction can be carried out in the presence of a base, such as 1,1,3,3-tetramethylguanidine, sodium hydride or sodium tert-butoxide, in a solvent, such as tetrahydrofuran, acetonitrile or dimethylformamide, at a temperature of between 0° C. and 80° C. The oxazolidinedione derivative of general formula (VII) thus obtained is subsequently converted to the compound of general formula (I) by aminolysis using an amine of general formula $R_8NH_2$, where $R_8$ is as defined in the general formula (I).

Scheme 2

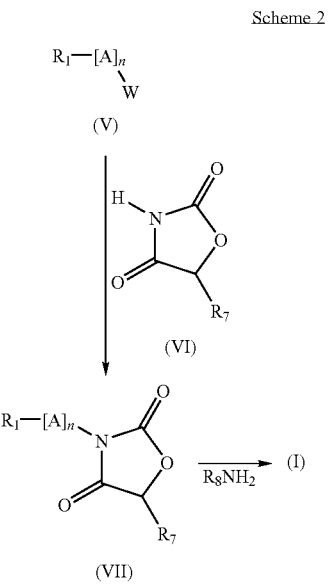

The compounds of general formula (I), (IV) and (VII) in which $R_1$ represents a group of aryl-aryl, aryl-heteroaryl, heteroaryl-aryl or heteroaryl-heteroaryl type can also be prepared by reaction of the corresponding compounds of general formula (I), (IV) or (VII) for which $R_2$ is substituted by a chlorine, bromine or iodine atom or by a triflate group in the position where the $R_4$ group has to be introduced with an aryl- or heteroarylboronic acid derivative according to the Suzuki reaction conditions (Chem. Rev., 1995, 95, 2457-2483) or with an aryl- or heteroaryltrialkylstannane derivative according to the Stille reaction conditions (Angew. Chem. Int. Ed., 1986, 25, 504-524).

The carbonates of general formula (III) can be prepared according to any method described in the literature, for example by reaction of an alcohol of general formula HOCHR$_7$COOR, where R represents a methyl or ethyl group, with phenyl or 4-nitrophenyl chloroformate in the presence of a base, such as triethylamine or diisopropylethylamine.

The compounds of general formulae (II), (V) and (VI) and the amines of general formula $R_8NH_2$, when their method of preparation is not described, are commercially available or are described in the literature or can be prepared according to various methods described in the literature or known to a person skilled in the art.

The compounds of general formula (IV) in which n, A, $R_1$ and $R_7$ are as defined in the general formula (I) and R represents a methyl or ethyl group are novel and also form part of the invention, the following compounds being excluded:
ethyl 2-[({[2-(5-hydroxy-1H-indol-3-yl)ethyl]amino}carbonyl)oxy]propanoate;
ethyl 2-[({[2-[5-(phenylmethoxy)-1H-indol-3-yl]ethyl]amino}carbonyl)oxy]propanoate.

The compounds of general formula (IV) are of use as synthetic intermediates for the preparation of the compounds of general formula (I).

The compounds of general formula (VII) in which n, A, $R_1$ and $R_7$ are as defined in the general formula (I) are novel and also form part of the invention, the following compounds being excluded:
2-[2-(2,4-dioxo-3-oxazolidinyl)ethyl]-1-methylpyridinium iodide;
2-[2-(2,4-dioxo-3-oxazolidinyl)ethyl]-5-ethyl-1-methylpyridinium iodide;
4-[2-(2,4-dioxo-3-oxazolidinyl)ethyl]-1-methylpyridinium iodide;
5-methyl-3-[2-(4-pyridyl)ethyl]-2,4-oxazolidinedione hydrochloride;
5-methyl-3-[2-(2-pyridyl)ethyl]-2,4-oxazolidinedione hydrochloride;
3-[5-(imidazo[1,2-a]pyridin-5-yl)pentyl]-2,4-oxazolidinedione;
3-[2-(5-methyl-4-thiazolyl)ethyl]-2,4-oxazolidinedione;
3-[2-(1H-pyrrol-2-yl)ethyl]-2,4-oxazolidinedione;
3-[2-(2-thienyl)ethyl]-2,4-oxazolidinedione;
3-[3-(2-thienyl)propyl]-2,4-oxazolidinedione;
3-[4-(2-thienyl)butyl]-2,4-oxazolidinedione;
5-methyl-3-[2-(2-thienyl)ethyl]-2,4-oxazolidinedione;
5-ethyl-3-[2-(2-thienyl)ethyl]-2,4-oxazolidinedione;
3-[2-(3-thienyl)ethyl]-2,4-oxazolidinedione;
3-[2-(5-methyl-2-thienyl)ethyl]-2,4-oxazolidinedione;
3-[2-(5-acetyl-2-thienyl)ethyl]-2,4-oxazolidinedione;
3-[2-(5-bromo-2-thienyl)ethyl]-2,4-oxazolidinedione;
5-[2-(2,4-dioxo-3-oxazolidinyl)ethyl]-2-thiophenecarbaldehyde;
3-[3-(1-indolinyl)propyl]-2,4-oxazolidinedione;
3-[3-(1-indolinyl)propyl]-5-methyl-2,4-oxazolidinedione;
3-[2-(2-pyridyl)ethyl]-2,4-oxazolidinedione;
3-[2-(5-ethyl-2-pyridyl)ethyl]-5-methyl-2,4-oxazolidinedione;
5-ethyl-3-[2-(5-ethyl-2-pyridyl)ethyl]-2,4-oxazolidinedione;
3-[2-(5-ethyl-2-pyridyl)ethyl]-5-isopropyl-2,4-oxazolidinedione;
3-[2-(4-pyridyl)ethyl]-2,4-oxazolidinedione;
5-ethyl-3-[2-(4-pyridyl)ethyl]-2,4-oxazolidinedione;
5-ethyl-3-[2-(2-pyridyl)ethyl]-2,4-oxazolidinedione;
5-isopropyl-3-[2-(4-pyridyl)ethyl]-2,4-oxazolidinedione;
5-isopropyl-3-[2-(2-pyridyl)ethyl]-2,4-oxazolidinedione;
3-[2-(5-ethyl-2-pyridyl)ethyl]-2,4-oxazolidinedione.

The compounds of general formula (VII) are of use as synthetic intermediates for the preparation of the compounds of general formula (I).

A subgroup of compounds of general formula (VII) is composed of the compounds for which:
n, A, $R_1$ and $R_7$ are as defined in the general formula (I) provided that:
when $R_2$ is a pyrrolyl, imidazo[1,2-a]pyridyl or indolinyl group, then $R_2$ is substituted by one or more $R_3$ and/or $R_4$ groups;
when $R_2$ is a pyridyl group, then $R_2$ is substituted by one or more $R_3$ and/or $R_4$ groups where $R_3$ is other than a methyl or than an ethyl;
when $R_2$ is a thienyl group, then $R_2$ is substituted by one or more $R_3$ and/or $R_4$ groups where $R_3$ is other than a bromine, than a methyl or than a CHO or COCH$_3$ group;
when $R_2$ is a thioazolyl group substituted by an $R_3$ group, then $R_3$ is other than a methyl.

The examples which will follow illustrate the preparation of a few compounds of the invention. These examples are not limiting and only illustrate the invention. The microanalyses, the IR and NMR spectra and/or the LC-MS (Liquid Chromatography coupled to Mass Spectroscopy) confirm the structures and the purities of the compounds obtained.

M.p. (° C.) represents the melting point in degrees Celsius.

The numbers shown in brackets in the titles of the examples correspond to those in the 1st column in the table below.

EXAMPLE 1 (COMPOUND NO. 3)

2-(methylamino)-2-oxoethyl 2-(6-phenylpyrid-3-yl) ethylcarbamate

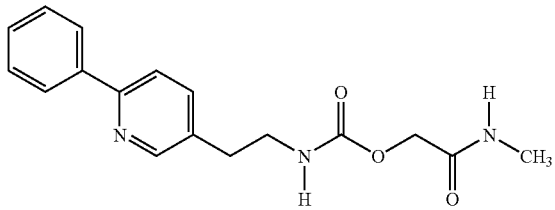

1.1. phenylmethyl 2-(6-phenylpyrid-3-yl)ethylcarbamate

A solution of 3.12 g (12.80 mmol) of 9-borabicyclo[3.3.1] nonane (BBN) in 100 ml of tetrahydrofuran is added dropwise, under an inert atmosphere, to a solution, cooled to approximately −10° C., of 4.5 g (25.60 mmol) of phenylmethyl ethenylcarbamate (Org. Proc. Res. & Develop.; 2002, 6, 74-77) in 25 ml of tetrahydrofuran while keeping the temperature of the reaction medium below −10° C. Stirring is continued at −10C for 1 hour and then at ambient temperature for 4 hours. 18 ml of an aqueous sodium hydroxide solution (3N) are added and stirring is continued for 1 hour. 4.0 g (17.1 mmol) of 5-bromo-2-phenylpyridine and 2.12 g (2.6 mmol) of $PdCl_2$(dppf).$CH_2Cl_2$ (dppf: 1,1'-bis(diphenylphosphino) ferrocene) are subsequently added. Stirring is continued at ambient temperature for 18 hours.

The reaction medium is cooled with a bath of ice-cold water and then 40 ml of a 2/1 mixture of a buffer solution (pH=7) and of 30% aqueous hydrogen peroxide solution are added dropwise. The mixture is left stirring at ambient temperature for 1 hour. The aqueous phase is separated and is then extracted three times with dichloromethane. The organic phases are combined and are washed successively with water and a saturated aqueous sodium chloride solution. The organic phase is dried over sodium sulphate and the filtrate is concentrated under reduced pressure. The residue thus obtained is purified by chromatography on silica gel, elution being carried out with a 20/80 mixture of ethyl acetate and of cyclohexane. 2.9 g of product are obtained in the form of a white solid.

M.p. (° C.): 118° C.

1.2. 2-(6-phenylpyrid-3-yl)ethanamine 9 ml of 33% hydrobromic acid in acetic acid are added dropwise to a solution, cooled to approximately 0° C., of 1.8 g (5.42 mmol) of phenylmethyl 2-(6-phenylpyrid-3-yl)ethylcarbamate, prepared in stage 1.1., in 50 ml of dichloromethane. Stirring is continued at ambient temperature for 2 hours. The mixture is concentrated under reduced pressure and the residue is taken up in dichloromethane and a saturated aqueous sodium hydrogencarbonate solution. The aqueous phase is separated and is extracted twice with ethyl acetate. The combined organic phases are washed with a saturated aqueous sodium chloride solution and dried over sodium sulphate, and the filtrate is concentrated under reduced pressure.

0.86 g of product is obtained in the form of an oil used as is in the following stage.

1.3. ethyl ({[2-(6-phenylpyrid-3-yl)ethyl]amino}carbonyl) oxyacetate

A solution of 0.85 g (4.29 mmol) of 2-(6-phenylpyrid-3-yl)ethanamine, prepared in stage 1.2., and of 1.25 g (5.58 mmol) of ethyl [(phenyloxycarbonyl)oxy]acetate (J. Med. Chem., 1999, 42, 277-290) in 40 ml of toluene is heated at 60° C. for 12 hours. The mixture is allowed to return to ambient temperature, the insoluble material is separated by filtration and the filtrate is concentrated under reduced pressure. The residue thus obtained is purifed by chromatography on silica gel, elution being carried out with a 30/70 mixture of ethyl acetate and of cyclohexane.

1.06 g of product are thus obtained in the form of an oil.

1.4. 2-(methylamino)-2-oxoethyl 2-(6-phenylpyrid-3-yl)ethylcarbamate 4.6 ml (9.17 mmol) of a solution of methylamine (2M) in tetrahydrofuran are added to a solution of 1.0 g (3.06 mmol) of ethyl ({[2-(6-phenylpyrid-3-yl)ethyl]amino}carbonyl)-oxyacetate, obtained in stage 1.3., in 6 ml of methanol. Stirring is continued at ambient temperature for 4 hours.

After concentrating under reduced pressure, the residue obtained is purified by chromatography on silica gel, elution being carried out with a 95/5 mixture of dichloromethane and of methanol. A white solid is obtained and is recrystallized from ethyl acetate.

0.510 g of product is obtained in the form of a white solid.
LC-MS: M+H=314 M.p. (° C.): 130-132° C. $^1$H NMR (CDCl$_3$) δ (ppm): 2.85 (d, 3H), 2.95 (t, 2H), 3.55 (q, 2H), 4.60 (s, 2H), 5.05 (broad s, 1H), 6.10 (broad s, 1H), 7.50 (m, 3H), 7.70 (m, 2H), 8.0 (d, 2H), 8.60 (s, 1H).

EXAMPLE 2 (COMPOUND NO. 56)

2-(methylamino)-2-oxoethyl 4-(1H-indol-1-yl)butyl-carbamate

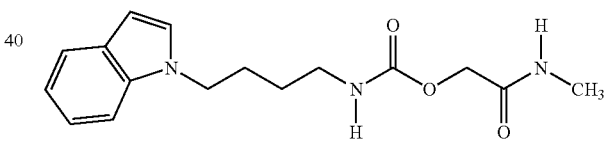

2.1. 1-(4-bromobutyl)-1H-indole 0.96 g (17.07 mmol) of sodium hydroxide is added in small portions to a solution, cooled by a bath of ice-cold water, of 2 g (17.07 mmol) of 1H-indole and of 1.15 ml (51.22 mmol) of 1,4-dibromobutane in 80 ml of dimethylformamide. The bath is removed and stirring is continued at ambient temperature for 15 hours.

After concentrating under reduced pressure, the residue is taken up in water and ethyl acetate. The aqueous phase is separated and extracted twice with ethyl acetate, the combined organic phases are washed with a saturated aqueous sodium chloride solution and dried over sodium sulphate, and the filtrate is concentrated under reduced pressure. The residue thus obtained is purified by chromatography on silica gel, elution being carried out with a 1/99 mixture of ethyl acetate and of cyclohexane.

3 g of product are obtained in the form of a yellow oil.

2.2. 3-[4-(1H-indol-1-yl)butyl]-1,3-oxazolidine-2,4-dione

A solution of 3 g (11.90 mmol) of 1-(4-bromobutyl)-1H-indole, prepared in stage 2.1., of 2.41 g (23.80 mmol) of 1,3-oxazolidin-2,4-dione (J. Med. Chem., 1991, 34, 1538-

1544) and of 2.74 g (23.80 mmol) of 1,1,3,3-tetramethylguanidine in 30 ml of tetrahydrofuran is brought to reflux for 14 hours under an inert atmosphere.

The mixture is concentrated under reduced pressure. The residue is taken up in ethyl acetate and water, the aqueous phase is separated and extracted twice with ethyl acetate, and the combined organic phases are washed with a saturated aqueous sodium chloride solution and dried over sodium sulphate. After evaporation of the solvent, the residue obtained is purified by chromatography on silica gel, elution being carried out with a 10/90 and then 20/80 mixture of ethyl acetate and of cyclohexane.

2 g of product are obtained in the form of a white solid.

2.3. 2-(methylamino)-2-oxoethyl 4-(1H-indol-1-yl)butylcarbamate

The procedure is as described in Example 1 (stage 1.4.). Starting from 0.90 g (3.31 mmol) of 3-[4-(1H-indol-1-yl)butyl]-1,3-oxazolidine-2,4-dione, obtained in stage 2.2., and from 5 ml (9.93 mmol) of a solution of methylamine (2M) in tetrahydrofuran, and after chromatography on silica gel, elution being carried out with a 98/2 mixture of dichloromethane and of methanol, 0.70 g of product is obtained in the form of an amorphous white solid.

LC-MS: M+H=304 M.p. (° C.): 64-67° C. $^1$H NMR (CDCl$_3$) δ (ppm): 1.50 (m, 2H), 1.90 (m, 2H), 2.80 (d, 3H), 3.20 (q, 2H), 4.20 (t, 2H), 4.55 (s, 2H), 5.95 (broad s, 1H), 6.10 (broad s, 1H), 6.50 (d, 1H), 7.20 (m, 3H), 7.40 (d, 1H), 7.70 (d, 1H).

EXAMPLE 3 (COMPOUND NO. 71)

2-amino-2-oxoethyl [5-(naphth-1-yl)pent-4-yn-1-yl] carbamate

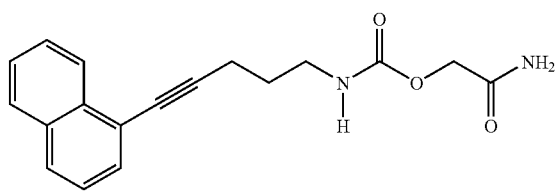

3.1. 5-(naphth-1-yl)pent-4-yn-1-ol

A solution of 0.59 g (7 mmol) of 4-pentyn-1-ol in 3 ml of acetonitrile is added dropwise under an argon atmosphere to a suspension of 1.78 g (7 mmol) of 1-iodonaphthalene, of 1.48 ml (10.5 mmol) of triethylamine, of 0.066 g (0.35 mmol) of cuprous iodide and of 0.147 g (0.21 mmol) of di(triphenylphosphine)palladium dichloride (Ph$_3$P)$_2$PdCl$_2$ in 4 ml of acetonitrile. The mixture is stirred at ambient temperature for 3 hours, 4 g of silica are then added and the mixture is evaporated to dryness. The product is purified by chromatography on silica gel, elution being carried out with an 80/20 and then 60/40 mixture of cyclohexane and of ethyl acetate, to produce 1.22 g of product in the form of a yellow oil.

3.2. 5-(naphth-1-yl)pent-4-yn-1-yl methanesulphonate

A solution of 0.85 g (7.42 mmol) of methanesulphonyl chloride in 5 ml of dichloromethane is added dropwise to a solution, cooled with an ice bath, of 1.2 g (5.71 mmol) of 5-(naphth-1-yl)pent-4-yn-1-ol, obtained in stage 3.1., and of 1.6 ml (11.4 mmol) of triethylamine in 12 ml of dichloromethane. The mixture is stirred at 0° C. for 1 hour and then at ambient temperature for 2 hours. 25 ml of water and 75 ml of dichloromethane are subsequently added. The organic phase is separated by settling and is washed with 25 ml of water and then with 25 ml of a saturated aqueous sodium chloride solution. It is dried over magnesium sulphate and evaporated to dryness to produce 1.68 g of product in the form of an orange oil used directly in the following stage.

3.3. 3-[5-(naphth-1-yl)pent-4-yn-1-yl]-1,3-oxazolidine-2,4-dione.

1.64 g (5.70 mmol) of 5-(naphth-1-yl)pent-4-yn-1-yl methanesulphonate, obtained in stage 3.2., and 0.72 g (7.1 mmol) of 1,3-oxazolidine-2,4-dione are dissolved in 9 ml of tetrahydrofuran. 1.3 g (11.4 mmol) of 1,1,3,3-tetramethylguanidine in solution in 3 ml of tetrahydrofuran are added. The mixture is heated at reflux overnight. 25 ml of ethyl acetate and 6 g of silica are added. The mixture is evaporated to dryness. The residue is purified by chromatography on silica gel, elution being carried out with a 90/10 and then 80/20 and 70/30 mixture of cyclohexane and of ethyl acetate, to produce 1.33 g of product in the form of a white solid.

M.p. (° C.): 99-101° C.

3.4. 2-amino-2-oxoethyl[5-(naphth-1-yl)pent-4-yn-1-yl]carbamate 0.75 g (2.56 mmol) of 3-[5-(naphth-1-yl)pent-4-yn-1-yl]-1,3-oxazolidine-2,4-dione, obtained in stage 3.3., is dissolved in 18 ml of a 7M solution of ammonia (126 mmol) in methanol. The mixture is left overnight at ambient temperature. 3 g of silica are subsequently added and the mixture is evaporated to dryness. The residue is purified by chromatography on silica gel, elution being carried out with a 98/2 and then 96/4 and 94/6 mixture of dichloromethane and of methanol. The product is subsequently recrystallized from a mixture of ethyl acetate and of diisopropyl ether to produce 0.59 g of product in the form of white crystals.

LC-MS: M+H=311 M.p. (° C.): 105-108° C. $^1$H NMR (CDCl$_3$) δ (ppm): 8.33 (d, 1H), 7.85 (m, 2H), 7.70-7.40 (m, 4H), 5.90 (broad m, 1H), 5.50 (broad m, 1H), 5.20 (broad m, 1H), 4.55 (s, 2H), 3.50 (m, 2H), 2.70 (t, 2H), 1.95 (m, 2H).

EXAMPLE 4 (COMPOUND NO. 29)

2-(methylamino)-2-oxoethyl 3-[3-(4-chlorophenyl)isoxazol-5-yl]propylcarbamate

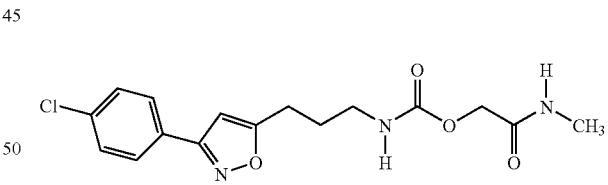

4.1. 3-[3-(4-chlorophenyl)isoxazol-5-yl]propan-1-ol 1.6 ml (11.5 mmol) of triethylamine are added dropwise to a solution, cooled with an ice bath, of 1.18 ml (12.6 mmol) of pent-4-yn-1-ol and of 2.0 g (10.5 mmol) of 4-chloro-N-hydroxybenzenecarboximidoyl chloride (J. Med. Chem., 1998, 41, 4556-4566) in 30 ml of dichloromethane. Reaction is allowed to take place at ambient temperature overnight. 50 ml of dichloromethane and 70 ml of water are added. The organic phase is separated and the aqueous phase is extracted with 2 times 50 ml of dichloromethane. The organic phases are subsequently washed with 2 times 70 ml of water and then with 70 ml of a saturated aqueous sodium chloride solution, dried over sodium sulphate and evaporated. The residue is purified by chromatography on silica gel, elution being carried out with a mixture of cyclohexane and of ethyl acetate, to produce 1.3 g (5.47 mmol) of product in the form of a white solid.

M.p. (° C.): 60-62° C.

4.2. 3-{3-[3-(4-chlorophenyl)isoxazol-5-yl]propyl}-1,3-oxazolidine-2,4-dione 0.5 ml (6.0 mmol) of methanesulphonyl chloride is added dropwise to a solution, cooled with an ice bath, of 1.30 g (5.47 mmol) of 3-[3-(4-chlorophenyl)isoxazol-5-yl]propan-1-ol, prepared in stage 4.1., and of 0.9 ml (7.11 mmol) of triethylamine in 70 ml of dichloromethane. The mixture is subsequently stirred at room temperature for 2 hours. 70 ml of water are added and the organic phase is separated. The aqueous phase is extracted with 2 times 70 ml of dichloromethane. The organic phases are subsequently washed with 100 ml of water and 100 ml of a saturated aqueous sodium chloride solution, dried over sodium sulphate and evaporated.

The residue is redissolved in 60 ml of tetrahydrofuran, and 0.9 g (8.9 mmol) of 1,3-oxazolidine-2,4-dione and 1.1 ml (8.7 mmol) of 1,1,3,3-tetramethylguanidine are added. The mixture is heated at 65° C. overnight. It is taken up in a mixture of 100 ml of water and of 100 ml of ethyl acetate. The organic phase is separated and the aqueous phase is extracted with 2 times 80 ml of ethyl acetate. The organic phases are washed with 100 ml of water and then with 100 ml of a saturated aqueous sodium chloride solution, dried over sodium sulphate and evaporated. The residue is purified by chromatography on silica gel, elution being carried out with a 90.5/0.5 mixture of dichloromethane and of methanol, to produce 1.0 g (3.1 mmol) of product in the form of a white solid.

4.3. 2-(methylamino)-2-oxoethyl 3-[3-(4-chlorophenyl)isoxazol-5-yl]propylcarbamate 0.6 g (1.87 mmol) of 3-{3-[3-(4-chlorophenyl)isoxazol-5-yl]propyl}-1,3-oxazolidine-2,4-dione, prepared in stage 4.2., is dissolved in a mixture of 8 ml of tetrahydrofuran and of 15 ml of methanol. 2.8 ml of a 2M solution of methylamine (5.6 mmol) in tetrahydrofuran are added. Reaction is allowed to take place at ambient temperature overnight and then the mixture is evaporated. The residue is purified by chromatography on silica gel, elution being carried out with a 98/2 and then 95/5 and 90/10 mixture of dichloromethane and of methanol. The product is recrystallized from a mixture of ethyl acetate and of methanol to produce 0.49 g (1.4 mmol) of white crystals.

LC-MS: M+H=352 M.p. (° C.): 158-160° C. $^1$H NMR (CDCl$_3$) δ (ppm): 7.75 (d, 2H), 7.45 (d, 2H), 6.35 (s, 1H), 6.10 (broad s, 1H), 5.00 (broad s, 1H), 4.60 (s, 2H), 3.35 (m, 2H), 2.85 (m+d, 5H), 2.05 (m, 2H).

EXAMPLE 5 (COMPOUND NO. 20)

2-(methylamino)-2-oxoethyl 3-[6-(4-chlorophenyl)pyrimidin-4-yl]propylcarbamate

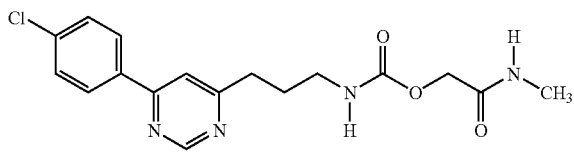

5.1. 1-(4-chlorophenyl)-6-(tetrahydro-2H-pyran-2-yloxy)hex-2-yn-1-ol 61.5 ml of 1.6M solution of n-butyllithium (98,4 mmol) in hexane are added dropwise to a solution, cooled to −78° C. under argon, of 13.25 g (78.8 mmol) of 2-(pent-4-yn-1-yloxy)tetrahydro-2H-pyran in 130 ml of anhydrous tetrahydrofuran. Stirring is continued at −78° C. for 1 hour and then a solution of 12.18 g (86.6 mmol) of 4-chlorobenzaldehyde in 40 ml of tetrahydrofuran is added dropwise. Stirring is continued at −78° C. for 2 hours and then the solution is reheated to 0° C. and is poured onto 300 ml of a saturated aqueous ammonium chloride solution. Extraction is carried out with 450 ml of ethyl acetate. The organic phase is washed with 50 ml of water and then with 50 ml of a saturated aqueous sodium chloride solution. The organic phase is dried over sodium sulphate and evaporated. The residue is purified by chromatography on silica gel, elution being carried out with a 70/30 mixture of n-hexane and of ethyl acetate, to produce 16.64 g (53.88 mmol) of product in the form of a colourless oil.

5.2. 1-(4-chlorophenyl)-6-(tetrahydro-2H-pyran-2-yloxy)hex-2-yn-1-one

A solution of 16.60 g (53.7 mmol) of 1-(4-chlorophenyl)-6-(tetrahydro-2H-pyran-2-yloxy)hex-2-yn-1-ol, prepared in stage 5.1., is added dropwise to a suspension, cooled with an ice bath, of 93 g (1.07 mol) of manganese dioxide in 500 ml of dichloromethane. Stirring is continued for 1.5 hours, then the mixture is filtered through celite and the filter cake is rinsed with dichloromethane. The filtrates are evaporated to produce 16.3 g (53.1 mmol) of product in the form of a yellowish oil.

5.3. 4-(4-chlorophenyl)-6-[3-(tetrahydro-2H-pyran-2-yloxy)propyl]pyrimidine

A mixture of 3.60 g (11.73 mmol) of 1-(4-chlorophenyl)-6-(tetrahydro-2H-pyran-2-yloxy)hex-2-yn-1-one, prepared in stage 5.2., of 9.45 g (117 mmol) of formamidine hydrochloride and of 25 g (234 mmol) of sodium carbonate in suspension in 108 ml of acetonitrile and 0.1 ml of water is stirred at 40° C. for 5 hours. The mixture is subsequently taken up in 600 ml of water and 400 ml of a saturated aqueous sodium carbonate solution. The organic phase is separated by settling, washed with 200 ml of water and 200 ml of a saturated aqueous sodium chloride solution, dried over sodium sulphate and evaporated. The residue is purified by chromatography on silica gel, elution being carried out with a 70/30 mixture of n-hexane and of ethyl acetate, to produce 3.22 g (9.67 mmol) of product in the form of a yellowish oil.

5.4. 3-[6-(4-chlorophenyl)pyrimidin-4-yl]propan-1-ol 3.22 g (9.67 mmol) of 4-(4-chlorophenyl)-6-[3-(tetrahydro-2H-pyran-2-yloxy)propyl]pyrimidine, prepared in stage 5.3., are dissolved in 32 ml of methanol, and 16 ml of a 4N solution of hydrochloric acid in dioxane are added. The mixture is stirred at ambient temperature for 1.5 hours and then 150 ml of a half-saturated aqueous sodium hydrogencarbonate solution are added portionwise. Extraction is carried out with 350 ml of ethyl acetate. The organic phase is washed with 50 ml of water and 50 ml of a saturated aqueous sodium chloride solution, dried over sodium sulphate and evaporated to produce 2.33 g (9.36 mmol) of product in the form of a white solid.

M.p. (° C.): 75-76° C.

5.5. 3-{3-[6-(4-chlorophenyl)pyrimidin-4-yl]propyl}-1,3-oxazolidine-2,4-dione 0.4 ml of a 40% solution of diethyl azodicarboxylate (0.9 mmol) in toluene is added to a solution, cooled with an ice bath, of 0.111 g (0.44 mmol) of 3-[6-(4-chlorophenyl)pyrimidin-4-yl]propan-1-ol, prepared in stage 5.4., of 0.077 g (0.76 mmol) of 1,3-oxazolidine-2,4-dione and of 0.235 g (0.89 mmol) of triphenylphosphine in 4 ml of tetrahydrofuran. The mixture is subsequently stirred at ambient temperature overnight. It is taken up in a mixture of ethyl acetate and of water. The organic phase is washed with a saturated aqueous sodium chloride solution, dried over sodium sulphate and evaporated. The residue is purified by chromatography on silica gel, elution being carried out with a 97/3 mixture of dichloromethane and of methanol, to produce 0.117 g (0.35 mmol) of product in the solid form.

5.6. 2-(methylamino)-2-oxoethyl 3-[6-(4-chlorophenyl)pyrimidin-4-yl]propylcarbamate 0.113 g (0.34 mmol) of 3-f{-3-[6-(4-chlorophenyl)pyrimidin-4-yl]propyl}-1,3-oxazolidine-2,4-dione, prepared in stage 5.5., is redissolved in a mixture of 4 ml of ethanol, 1 ml of methanol and 1 ml of dichloromethane. 2 ml of an 8M solution of methylamine (16 mmol) in ethanol are added. The mixture is stirred at ambient temperature for 2 hours and is then evaporated. The solid residue is taken up in diethyl ether to produce 0.127 g (0.34 mmol) of product in the form of a white solid.

LC-MS: M+H=363 M.p. (° C.): 147-149° C. $^1$H NMR (CDCl$_3$) δ (ppm): 9.15 (s, 1H), 8.05 (d, 2H), 7.65 (s, 1H), 7.55 (d, 2H), 6.15 (broad s, 1H), 5.30 (broad s, 1H), 4.55 (s, 2H), 3.35 (m, 2H), 2.85 (m+d, 5H), 2.10 (m, 2H).

The chemical structures and the physical properties of a few compounds according to the invention are illustrated in the following Table 1.

In this table:
- all the compounds are in the free base form,
- isopropyl, n-butyl and t-butyl respectively represent isopropyl, linear butyl and tert-butyl groups.

TABLE 1

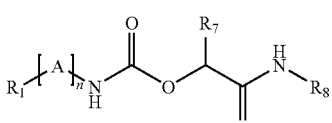

(I)

| No. | R$_1$ | [A]$_n$ | R$_7$ | R$_8$ | M.p. (° C.) (M + H) |
|---|---|---|---|---|---|
| 1. | 5-phenylpyrid-2-yl | CH$_2$ | H | CH$_3$ | 136-138 |
| 2. | 5-phenylpyrid-2-yl | (CH$_2$)$_2$ | H | CH$_3$ | (314) |
| 3. | 6-phenylpyrid-3-yl | (CH$_2$)$_2$ | H | CH$_3$ | 130-132 |
| 4. | 6-phenylpyridazin-3-yl | (CH$_2$)$_2$ | H | CH$_3$ | 159-161 |
| 5. | 2-phenylpyrimidin-5-yl | (CH$_2$)$_2$ | H | CH$_3$ | 125-127 |
| 6. | 5-phenylpyrimidin-2-yl | (CH$_2$)$_2$ | H | CH$_3$ | 150-152 |
| 7. | 6-(4-Cl-phenyl)pyrimidin-4-yl | (CH$_2$)$_2$ | H | CH$_3$ | 139-141 |
| 8. | 6-(4-Cl-phenyl)-2-methyl-pyrimidin-4-yl | (CH$_2$)$_2$ | H | CH$_3$ | 140-142 |
| 9. | 6-(4-Cl-phenyl)-2-(dimethylamino)-pyrimidin-4-yl | (CH$_2$)$_2$ | H | CH$_3$ | 131-133 |
| 10. | isoquinolin-7-yl | (CH$_2$)$_2$ | H | CH$_3$ | 134-136 |
| 11. | 4-phenylimidazol-1-yl | (CH$_2$)$_2$ | H | CH$_3$ | 111-113 |
| 12. | 2-phenyloxazol-4-yl | (CH$_2$)$_2$ | H | CH$_3$ | 94-98 |
| 13. | 5-(4-Cl-phenyl)isoxazol-3-yl | (CH$_2$)$_2$ | H | CH$_3$ | 150-152 |
| 14. | 3-(4-Cl-phenyl)-1-methyl-1H-pyrazol-5-yl | (CH$_2$)$_2$ | H | CH$_3$ | 125-127 |
| 15. | 5-phenyl-1,2,4-oxadiazol-3-yl | (CH$_2$)$_2$ | H | CH$_3$ | 131-135 |
| 16. | pyrid-2-yl | (CH$_2$)$_3$ | H | H | 114-115 |
| 17. | pyrid-3-yl | (CH$_2$)$_3$ | H | H | 105-107 |
| 18. | pyrid-4-yl | (CH$_2$)$_3$ | H | H | 161-162 |
| 19. | pyrimidin-5-yl | (CH$_2$)$_3$ | H | H | 119-121 |
| 20. | 6-(4-Cl-phenyl)pyrimidin-4-yl | (CH$_2$)$_3$ | H | CH$_3$ | 147-149 |
| 21. | 6-(4-Cl-phenyl)-2-methyl-pyrimidin-4-yl | (CH$_2$)$_3$ | H | CH$_3$ | (377) |
| 22. | 6-(4-Cl-phenyl)-2-(dimethylamino)-pyrimidin-4-yl | (CH$_2$)$_3$ | H | CH$_3$ | 150-152 |
| 23. | quinolin-2-yl | (CH$_2$)$_3$ | H | H | 117-119 |
| 24. | quinolin-4-yl | (CH$_2$)$_3$ | H | H | 150-152 |
| 25. | isoquinolin-1-yl | (CH$_2$)$_3$ | H | H | 123-124 |
| 26. | isoquinolin-4-yl | (CH$_2$)$_3$ | H | H | 154-156 |
| 27. | 5-(4-Cl-phenyl)isoxazol-3-yl | (CH$_2$)$_3$ | H | CH$_3$ | 138-140 |
| 28. | 3-(4-Cl-phenyl)isoxazol-5-yl | (CH$_2$)$_3$ | H | H | 176-178 |
| 29. | 3-(4-Cl-phenyl)isoxazol-5-yl | (CH$_2$)$_3$ | H | CH$_3$ | 158-160 |
| 30. | 3-(4-phenylphenyl)isoxazol-5-yl | (CH$_2$)$_3$ | H | CH$_3$ | 198-200 |
| 31. | 3-(naphth-2-yl)isoxazol-5-yl | (CH$_2$)$_3$ | H | CH$_3$ | 143-145 |
| 32. | 3-(4-Cl-phenyl)-1-methyl-1H-pyrazol-5-yl | (CH$_2$)$_3$ | H | CH$_3$ | (365) |
| 33. | 4-phenylimidazol-1-yl | (CH$_2$)$_3$ | H | CH$_3$ | 96-98 |
| 34. | benzimidazol-1-yl | (CH$_2$)$_3$ | H | CH$_3$ | 154-156 |
| 35. | pyrid-2-yl | (CH$_2$)$_4$ | H | H | 141-143 |
| 36. | pyrid-3-yl | (CH$_2$)$_4$ | H | H | 131-133 |
| 37. | pyrid-4-yl | (CH$_2$)$_4$ | H | H | 124-126 |
| 38. | pyrimidin-5-yl | (CH$_2$)$_4$ | H | H | 139-141 |
| 39. | 6-(4-Cl-phenyl)pyrimidin-4-yl | (CH$_2$)$_4$ | H | CH$_3$ | 101-103 |
| 40. | 6-(4-Cl-phenyl)-2-methyl-pyrimidin-4-yl | (CH$_2$)$_4$ | H | CH$_3$ | 118-120 |
| 41. | 6-(4-Cl-phenyl)-2-cyclopropyl-pyrimidin-4-yl | (CH$_2$)$_4$ | H | CH$_3$ | 118-120 |
| 42. | 6-(4-Cl-phenyl)-2-(dimethylamino)-pyrimidin-4-yl | (CH$_2$)$_4$ | H | CH$_3$ | 120-122 |
| 43. | quinolin-2-yl | (CH$_2$)$_4$ | H | H | 131-133 |
| 44. | quinolin-4-yl | (CH$_2$)$_4$ | H | H | (302) |
| 45. | isoquinolin-1-yl | (CH$_2$)$_4$ | H | H | 119-121 |
| 46. | isoquinolin-4-yl | (CH$_2$)$_4$ | H | H | 154-156 |
| 47. | 5-(4-Cl-phenyl)isoxazol-3-yl | (CH$_2$)$_4$ | H | CH$_3$ | 130-132 |
| 48. | 3-(4-Cl-phenyl)isoxazol-5-yl | (CH$_2$)$_4$ | H | CH$_3$ | 138-140 |
| 49. | 3-(4-phenylphenyl)isoxazol-5-yl | (CH$_2$)$_4$ | H | CH$_3$ | 193-195 |
| 50. | 3-(naphth-2-yl)isoxazol-5-yl | (CH$_2$)$_4$ | H | CH$_3$ | 158-160 |
| 51. | 3-(4-Cl-phenyl)-1-methyl-1H-pyrazol-5-yl | (CH$_2$)$_4$ | H | CH$_3$ | 144-146 |
| 52. | 4-phenylimidazol-1-yl | (CH$_2$)$_4$ | H | H | 113-115 |
| 53. | 4-phenylimidazol-1-yl | (CH$_2$)$_4$ | H | CH$_3$ | 109-111 |
| 54. | benzimidazol-1-yl | (CH$_2$)$_4$ | H | CH$_3$ | 114-116 |
| 55. | indol-1-yl | (CH$_2$)$_4$ | H | H | 100-102 |
| 56. | indol-1-yl | (CH$_2$)$_4$ | H | CH$_3$ | 64-67 |
| 57. | pyrrolo[2,3-b]pyrid-1-yl | (CH$_2$)$_4$ | H | H | 102-104 |
| 58. | pyrrolo[2,3-b]pyrid-1-yl | (CH$_2$)$_4$ | H | CH$_3$ | 52-54 |
| 59. | tetrahydroisoquinolin-2-yl | (CH$_2$)$_4$ | H | CH$_3$ | (320) |
| 60. | 2-oxo-3,4-dihydro-quinolin-1(2H)-yl | (CH$_2$)$_4$ | H | H | (320) |
| 61. | 2-oxo-3,4-dihydro-quinolin-1(2H)-yl | (CH$_2$)$_4$ | H | CH$_3$ | (334) |
| 62. | pyrid-2-yl | (CH$_2$)$_5$ | H | H | 77-79 |
| 63. | pyrid-4-yl | (CH$_2$)$_5$ | H | H | 155-157 |
| 64. | pyrimidin-5-yl | (CH$_2$)$_5$ | H | H | 115-117 |

TABLE 1-continued $$R_1 \underset{H}{\overset{}{\text{–}}} [A]_n \underset{H}{\overset{}{\text{–}}} \underset{\overset{\|}{O}}{C} \text{–} O \text{–} \underset{\overset{\|}{O}}{\overset{R_7}{C}} \text{–} \underset{H}{\overset{}{\text{–}}} R_8 \quad (I)$$

| No. | $R_1$ | $[A]_n$ | $R_7$ | $R_8$ | M.p. (°C.) (M+H) |
|---|---|---|---|---|---|
| 65. | quinolin-2-yl | $(CH_2)_5$ | H | H | (316) |
| 66. | quinolin-4-yl | $(CH_2)_5$ | H | H | 115-117 |
| 67. | isoquinolin-1-yl | $(CH_2)_5$ | H | H | 134-135 |
| 68. | isoquinolin-4-yl | $(CH_2)_5$ | H | H | (316) |
| 69. | naphth-1-yl | $C≡CCH_2$ | H | H | 132-134 |
| 70. | naphth-1-yl | $C≡CCH_2$ | H | $CH_3$ | 107-109 |
| 71. | naphth-1-yl | $C≡C(CH_2)_3$ | H | H | 105-106 |
| 72. | naphth-1-yl | $C≡C(CH_2)_3$ | H | $CH_3$ | 73-76 |
| 73. | 4-F-naphth-1-yl | $C≡C(CH_2)_3$ | H | $CH_3$ | 96-98 |
| 74. | 3-(pyrid-3-yl)isoxazol-5-yl | $(CH_2)_3$ | H | $CH_3$ | 133-135 |
| 75. | 3-(4-methoxy-naphth-1-yl)isoxazol-5-yl | $(CH_2)_3$ | H | $CH_3$ | 95-97 |

The compounds of the invention have formed the subject of pharmacological trials which make it possible to determine their inhibitory effect on the enzyme FAAH (Fatty Acid amido Hydrolase).

The inhibitory activity was demonstrated in a radioenzymatic test based on the measurement of the product of hydrolysis ((1-$^3$H)ethanolamine) of ((1-$^3$H)ethanolamine)-anandamide by FAAH (*Life Sciences* (1995), 56, 1999-2005 and *Journal of Pharmacology and Experimental Therapeutics* (1997), 283, 729-734). Thus, mouse brains (minus the cerebellum) are removed and stored at −80° C. The membrane homogenates are prepared at the time of use by homogenization of the tissues with a Polytron in a 10 mM Tris-HCl buffer (pH 8.0) comprising 150 mM NaCl and 1 mM EDTA. The enzymatic reaction is subsequently carried out in 70 μl of buffer comprising bovine serum albumin free from fatty acids (1 mg/ml). The test compounds, at various concentrations, the ((1-$^3$H)ethanolamine)-anandamide (specific activity of 15-20 Ci/mmol), diluted to 10 μM with non-radiolabelled anandamide, and the membrane preparation (400 μg of frozen tissue per assay) are successively added. After 15 minutes at 25° C., the enzymatic reaction is halted by addition of 140 μl of chloroform/methanol (2:1). The mixture is stirred for 10 minutes and is then centrifuged at 3500 g for 15 minutes. An aliquot (30 μl) of the aqueous phase comprising the (1-$^3$H) ethanolamine is counted by liquid scintillation.

Under these conditions, the most active compounds of the invention exhibit $IC_{50}$ values (concentration which inhibits the control enzymatic activity of FAAH by 50%) of between 0.001 and 1 μM.

For example, compound No. 68 in the table exhibits an $IC_{50}$ of 0.267 μM.

It is therefore apparent that the compounds according to the invention have an inhibitory activity on the enzyme FAAH.

The in vivo activity of the compounds of the invention was evaluated in a test for analgesia. Thus, the intraperitoneal (i.p.) administration of PBQ (phenylbenzoquinone, 2 mg/kg in a 0.9% sodium chloride solution comprising 5% of ethanol) to male OF1 mice weighing 25 to 30 g causes abdominal tractions, on average 30 twisting or contracting motions during the period from 5 to 15 minutes after injection. The test compounds are administered, orally (p.o.) or intraperitoneally (i.p.) in suspension in 0.5% Tween 80, 60 minutes or 120 minutes before the administration of PBQ. Under these conditions, the most powerful compounds of the invention reduce by 35 to 70% the number of tractions induced by the PBQ, within a range of doses of between 1 and 30 mg/kg.

For example, compound No. 48 in the table reduces by 53% and by 62% the number of tractions induced by the PBQ, at a dose of 10 mg/kg p.o., at 60 minutes and at 120 minutes respectively.

The enzyme FAAH (*Chemistry and Physics of Lipids*, (2000), 108, 107-121) catalyses the hydrolysis of endogenous derivatives of amides and esters of various fatty acids, such as N-arachidonoylethanolamine (anandamide), N-palmitoylethanolamine, N-oleoylethanolamine, oleamide or 2-arachidonoylglycerol. These derivatives have various pharmacological activities by interacting, inter alia, with the cannabinoid and vanilloid receptors.

The compounds of the invention block this decomposition pathway and increase the tissue level of these endogenous substances. They can therefore be used in the prevention and treatment of pathologies in which endogenous cannabinoids and/or any other substrate metabolized by the enzyme FAAH are involved.

Mention may be made, for example, of the following diseases and conditions:

Pain, in particular acute or chronic pain of neurogenic type: migraine, neuropathic pain, including forms associated with the herpes virus and with diabetes;

acute or chronic pain associated with inflammatory diseases: arthritis, rheumatoid arthritis, osteoarthritis, spondylitis, gout, vasculitis, Crohn's disease, irritable bowel syndrome;

acute or chronic peripheral pain;

dizziness, vomiting, nausea, in particular resulting from chemotherapy;

eating disorders, in particular anorexia and cachexia of various natures;

neurological and psychiatric pathologies: tremors, dyskinesias, dystonias, spasticity, obsessive-compulsive behaviour, Tourette's syndrome, all forms of depression and of anxiety of any nature and origin, mood disorders, psychoses;

acute and chronic neurodegenerative diseases: Parkinson's disease, Alzheimer's disease, senile dementia, Huntington's chorea, lesions related to cerebral ischaemia and to cranial and medullary trauma;

epilepsy;

sleep disorders, including sleep apnoea;

cardiovascular diseases, in particular hypertension, cardiac arrhythmias, arteriosclerosis, heart attack, cardiac ischaemia;

renal ischaemia;

cancers: benign skin tumours, brain tumours and papillomas, prostate tumours, cerebral tumours (glioblastomas, medulloepitheliomas, medulloblastomas, neuroblastomas, tumours of embryonic origin, astrocytomas, astroblastomas, ependymomas, oligodendrogliomas, plexus tumour, neuroepitheliomas, epiphyseal tumour, ependymoblastomas, malignant meningiomas, sarcomatosis, malignant melanomas, schwannomas);

disorders of the immune system, in particular autoimmune diseases: psoriasis, lupus erythematosus, diseases of the connective tissue or collagen diseases, Sjögren's syndrome, ankylosing spondylitis, undifferentiated spondylitis, Behcet's disease, autoimmune haemolytic anaemia, multiple sclerosis, amyotrophic lateral sclerosis, amyloidosis, graft rejection, diseases affecting the plasmocytic line;

allergic diseases; immediate or delayed hypersensitivity, allergic rhinitis or conjunctivitis, contact dermatitis;

parasitic, viral or bacterial infectious diseases: AIDS, meningitis;

inflammatory diseases, in particular joint diseases: arthritis, rheumatoid arthritis, osteoarthritis, spondylitis, gout, vasculitis, Crohn's disease, irritable bowel syndrome;

osteoporosis;

eye conditions: ocular hypertension, glaucoma;

pulmonary conditions: diseases of the respiratory tracts, bronchospasm, coughing, asthma, chronic bronchitis, chronic obstruction of the respiratory tract, emphysema;

gastrointestinal diseases: irritable bowel syndrome, inflammatory intestinal disorders, ulcers, diarrhoea;

urinary incontinence and bladder inflammation.

The use of a compound of formula (I), in the base or pharmaceutically acceptable salt, hydrate or solvate form, in the preparation of a medicament intended to treat the abovementioned pathologies forms an integral part of the invention.

Another subject-matter of the invention is medicaments which comprise a compound of formula (I) or a pharmaceutically acceptable salt, hydrate or solvate of the compound of formula (I). These medicaments are used in therapeutics, in particular in the treatment of the abovementioned pathologies.

According to another of its aspects, the present invention relates to pharmaceutical compositions including, as active principle, at least one compound according to the invention. These pharmaceutical compositions comprise an effective dose of a compound according to the invention or a pharmaceutically acceptable salt, hydrate or solvate of the said compound and optionally one or more pharmaceutically acceptable excipients.

The said excipients are chosen, depending on the pharmaceutical form and the method of administration desired, from the usual excipients which are known to a person skilled in the art.

In the pharmaceutical compositions of the present invention for oral, sublingual, subcutaneous, intramuscular, intravenous, topical, local, intrathecal, intranasal, transdermal, pulmonary, ocular or rectal administration, the active principle of formula (I) above or its optional salt, solvate or hydrate can be administered in a single-dose administration form, as a mixture with conventional pharmaceutical excipients, to animals and to man for the prophylaxis or the treatment of the above disorders or diseases.

Appropriate single-dose administration forms comprise oral forms, such as tablets, soft or hard gelatin capsules, powders, granules, chewing gums and oral solutions or suspensions, forms for sublingual, buccal, intratracheal, intraocular or intranasal administration or for administration by inhalation, forms for subcutaneous, intramuscular or intravenous administration and forms for rectal or vaginal administration. For topical application, the compounds according to the invention can be used in creams, ointments or lotions.

By way of example, a single-dose adminstration form of a compound according to the invention in the form of a tablet can comprise the following components:

| | |
|---|---|
| Compound according to the invention | 50.0 mg |
| Mannitol | 223.75 mg |
| Croscarmellose sodium | 6.0 mg |
| Maize starch | 15.0 mg |
| Hydroxypropylmethylcellulose | 2.25 mg |
| Magnesium stearate | 3.0 mg |

The said single-dose forms comprise a dose which makes possible a daily administration of 0.01 to 20 mg of active principle per kg of body weight, depending upon the pharmaceutical dosage form.

There may be specific cases where higher or lower dosages are appropriate; such dosages also come within the invention. According to the usual practice, the dosage appropriate to each patient is determined by the doctor according to the method of administration, the weight and the response of the said patient.

According to another of its aspects, the invention also relates to a method for the treatment of the pathologies indicated above which comprises the administration of an effective dose of a compound according to the invention, of one of its pharmaceutically acceptable salts or of a solvate or of a hydrate of the said compound.

What is claimed is:

1. A compound according to the general formula (I):

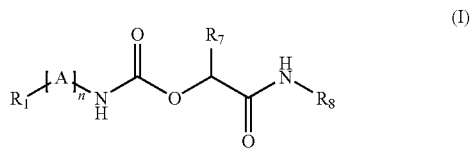

wherein A is selected from the group comprising X, Y or Z, and;

X represents a methylene group optionally substituted by one or two $C_{1-6}$-alkyl, $C_{3-7}$-cycloalkyl or $C_{3-7}$-cycloalkyl-$C_{1-3}$-alkylene groups;

Y represents either a $C_2$-alkenylene group optionally substituted by one or two $C_{1-6}$-alkyl, $C_{3-7}$-cycloalkyl or $C_{3-7}$-cycloalkyl-$C_{1-3}$-alkylene groups; or a $C_2$-alkynylene group;

Z represents a group of formula:

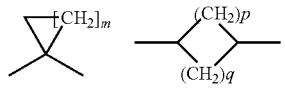

m represents an integer ranging from 1 to 5;

p and q represent integers and are defined such that p+q is a number ranging from 1 to 5;

n represents an integer ranging from 1 to 7;

$R_1$ is an $R_2$ group optionally substituted by one or more $R_3$ and/or $R_4$ groups;

$R_2$ is a pyrimidinyl group;

$R_3$ is selected from the group consisting of halogen atoms, cyano, nitro, $C_{1-6}$-alkyl, $C_{3-7}$-cycloalkyl, $C_{1-6}$-alkoxy, hydroxyl, $C_{1-6}$-thioalkyl, $C_{1-6}$-fluoroalkyl, $C_{1-6}$-fluoroalkoxy, $C_{1-6}$-fluorothioalkyl, $NR_5R_6$, $NR_5COR_6$, $NR_5CO_2R_6$, $NR_5SO_2R_6$, $COR_5$, $CO_2R_5$, $CONR_5R_6$, $SO_2R_5$, $SO_2NR_5R_6$ and phenyl groups, the phenyl group optionally substituted by one or more halogen atoms;

$R_4$ is selected from the group consisting of phenyl, phenyloxy, benzyloxy, naphthyl, pyridyl, pyrimidinyl, pyridazinyl and pyrazinyl groups; it being possible for the $R_4$ group or groups to be substituted by one or more $R_3$ groups which are identical to or different from one another;

$R_5$ and $R_6$ represent, independently of one another, a hydrogen atom or a $C_{1-6}$-alkyl group or, with the atom or atoms which carry them, form a ring chosen from the group consisting of an azetidine, pyrrolidine, piperidine, morpholine, thiomorpholine, azepine or piperazine ring, this ring optionally being substituted by a $C_{1-6}$-alkyl or benzyl group;

$R_7$ represents a hydrogen atom or a $C_{1-6}$-alkyl group, and $R_8$ represents a hydrogen atom or a $C_{1-6}$-alkyl, $C_{3-7}$-cycloalkyl or $C_{3-7}$-cycloalkyl-$C_{1-3}$-alkylene group; or a salt thereof.

2. The compound as recited in claim 1, wherein:

A is chosen from one or more groups X or Y;

X represents a methylene group;

Y represents a $C_2$-alkynylene group;

n represents an integer ranging from 1 to 5;

$R_3$ is selected from the group consisting of halogen atoms or $C_{1-6}$-alkyl, $C_{3-7}$-cycloalkyl, $C_{1-6}$-alkoxy, $NR_5R_6$ and phenyl groups;

$R_4$ is selected from the group consisting of phenyl, naphthyl and pyridyl groups; it being possible for the $R_4$ group or groups to be substituted by one or more $R_3$ groups which are identical to or different from one another;

$R_5$ and $R_6$ represent, independently of one another, a $C_{1-6}$-alkyl group;

$R_7$ represents a hydrogen atom or a $C_{1-6}$-alkyl group; and $R_8$ represents a hydrogen atom or a $C_{1-6}$-alkyl, $C_{3-7}$-cycloalkyl or $C_{3-7}$-cycloalkyl-$C_{1-3}$-alkylene group;

or a pharmaceutically acceptable salt thereof.

3. The compound as recited in claim 2 wherein $R_2$ is pyrimidinyl, which is substituted by $R_3$ and/or $R_4$ groups, wherein $R_3$ and $R_4$ are as defined in claim 2.

4. The compound as recited in claim 3 wherein:

$R_7$ represents a hydrogen atom; and $R_8$ represents a hydrogen atom or a $C_{1-6}$-alkyl group; or a pharmaceutically acceptable salt thereof.

5. A process for the preparation of the compound of formula (I) as recited in claim 1 comprising converting the carbamate ester of general formula (IV)

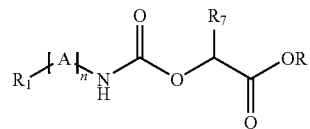

to the compound of formula (I) by aminolysis using an amine of general formula $R_8NH_2$, in which A, n, $R_1$, $R_7$ and $R_8$ are as recited in claim 1.

6. A process for the preparation of the compound of formula (I) as recited in claim 1 comprising converting the oxazolidinedione derivative of general formula (VII)

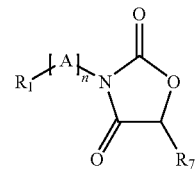

to the compound of formula (I) by aminolysis, using an amine of general formula $R_8NH_2$, in which in which A, n, $R_1$, $R_7$ and $R_8$ are as defined in claim 1.

7. A pharmaceutical composition comprising the compound of claim 1, or a pharmaceutically acceptable salt thereof, and one or more pharmaceutically acceptable excipients.

* * * * *

UNITED STATES PATENT AND TRADEMARK OFFICE
CERTIFICATE OF CORRECTION

PATENT NO. : 7,645,757 B2  
APPLICATION NO. : 11/464355  
DATED : January 12, 2010  
INVENTOR(S) : Ahmed Abouabdellah et al.

Page 1 of 1

It is certified that error appears in the above-identified patent and that said Letters Patent is hereby corrected as shown below:

On the Title page, in field (56), in column 1, under "U.S. Patent Documents", line 1, delete "Shapro" and insert -- Shapiro --, therefor.

On the Title page, in field (56), in column 2, under "Other Publications", line 18, delete "Oxazolidinedionos," and insert -- Oxazolidinediones, --, therefor.

On the Title page, in field (57), in column 2, in "Abstract", line 9, Excluding Structure, before "a salt" delete "alkylene group;".

On the Title page, in field (57), in column 2, in "Abstract", line 11, delete "the attached specification." and insert -- the specification. --, therefor.

In column 2, line 17, delete "benzoxazolyl" and insert -- benzoxazolyl, --, therefor.

In column 8, line 34, delete "formula (II)" and insert -- formula (III) --, therefor.

In column 11, line 29, delete "-10C" and insert -- -10°C --, therefor.

In column 17, line 14, delete "3-f{-3-[6-(4-chlorophenyl)" and insert -- 3-{-3-[6-(4-chlorophenyl) --, therefor.

In column 19, line 19, delete "105-106" and insert -- 105-108 --, therefor.

In column 24, line 29, in claim 6, delete "in which in which" and insert -- in which --, therefor.

Signed and Sealed this  
First Day of February, 2011

David J. Kappos  
*Director of the United States Patent and Trademark Office*